United States Patent [19]

Kusano et al.

[11] Patent Number: 4,654,006
[45] Date of Patent: Mar. 31, 1987

[54] DENTURE BASE PROVIDED WITH RUBBER-LIKE RESILIENT LINING LAYER AND PROCESS FOR PRODUCING THE SAME

[75] Inventors: Takae Kusano; Masato Ueno; Masanori Hirakiuchi, all of Hiroshima, Japan

[73] Assignees: Molten Corporation; Fourbrain Kabushiki Kaisha, both of Hiroshima, Japan

[21] Appl. No.: 845,295

[22] Filed: Mar. 28, 1986

[30] Foreign Application Priority Data

Mar. 29, 1985 [JP] Japan .................................. 60-67787
May 9, 1985 [JP] Japan .................................. 60-99043
May 9, 1985 [JP] Japan .................................. 60-99044

[51] Int. Cl.$^4$ ............................................. A61C 13/02
[52] U.S. Cl. ...................... 433/168.1; 264/17; 427/2; 428/515; 428/518; 428/520; 433/199.1; 433/171; 433/201.1; 523/120
[58] Field of Search ............... 433/199.1, 171, 201.1, 433/168.1; 264/17; 427/2; 428/515, 518, 520; 523/120

[56] References Cited

U.S. PATENT DOCUMENTS

| | | | |
|---|---|---|---|
| 2,457,114 | 12/1948 | Amenta | 18/55.1 |
| 3,083,459 | 4/1963 | McMurry et al. | 32/2 |
| 3,251,910 | 5/1966 | Barnhart | 264/17 |
| 3,628,988 | 12/1971 | Stol | 117/63 |
| 3,667,123 | 6/1972 | Huey | 32/2 |
| 3,727,309 | 4/1973 | Huey | 32/2 |
| 3,886,559 | 6/1975 | Reifke | 32/2 |
| 3,930,076 | 12/1975 | Kliment | 427/353 |
| 3,969,303 | 7/1976 | Prosen | 260/31.8 |
| 4,024,636 | 5/1977 | Colpitts et al. | 32/2 |
| 4,251,215 | 2/1981 | May et al. | 433/168 |
| 4,484,894 | 11/1984 | Masuhara et al. | 433/168 |

Primary Examiner—Lorenzo B. Hayes
Attorney, Agent, or Firm—Armstrong, Nikaido, Marmelstein & Kubovcik

[57] ABSTRACT

In accordance with the present invention, there can be provided a denture base for a dental prosthesis comprising a body having an inner surface to be in contact with patient's alveolus ridge; a lining layer covering the inner surface of the body; and an adhesive agent for bonding the lining layer to the inner surface of the body; wherein the body is made of polymethyl methacrylate; the lining layer is made of a rubber-like resilient material comprising an olefin thermoplastic elastomer; and the adhesive agent contains a copolymer comprising an olefin and methyl methacrylate. The denture base has an advantage that adhesive force between the lining layer and the body is strong, and the lining layer has suitable hardness for supporting the dental prosthesis.

11 Claims, 40 Drawing Figures

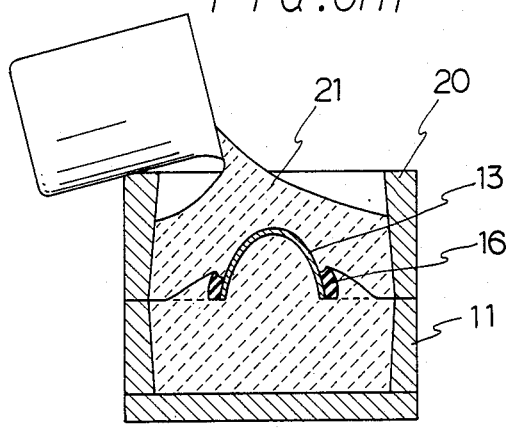
FIG.6H1
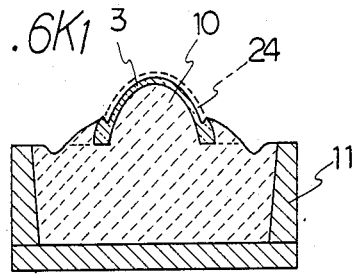
FIG.6K1
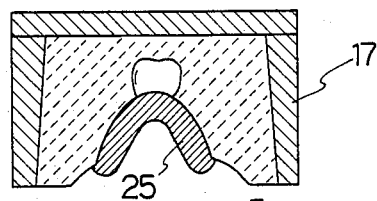
FIG.6L1
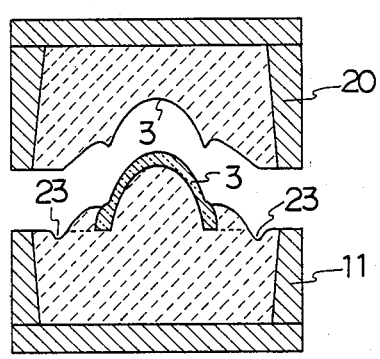
FIG.6I1
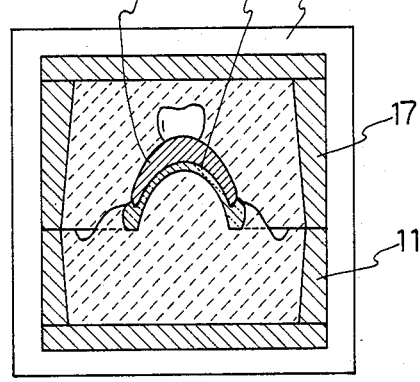
FIG.6M1
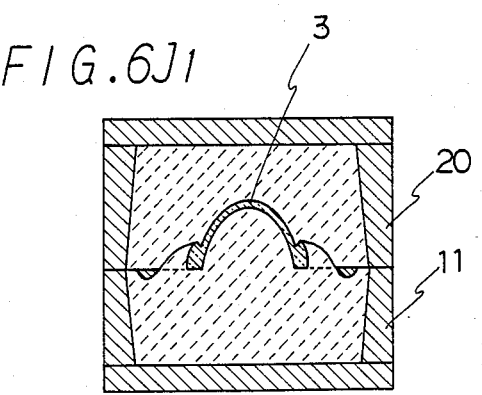
FIG.6J1
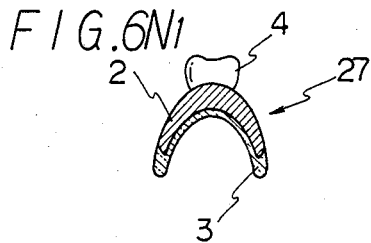
FIG.6N1

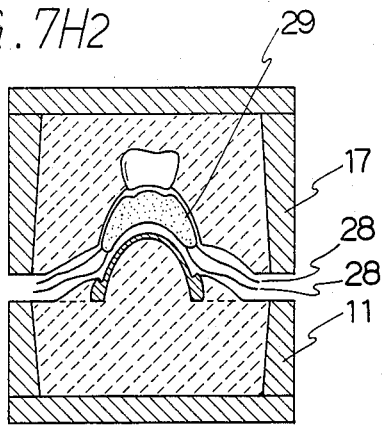
FIG.7H2
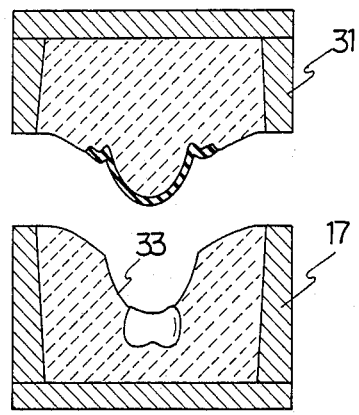
FIG.7K2
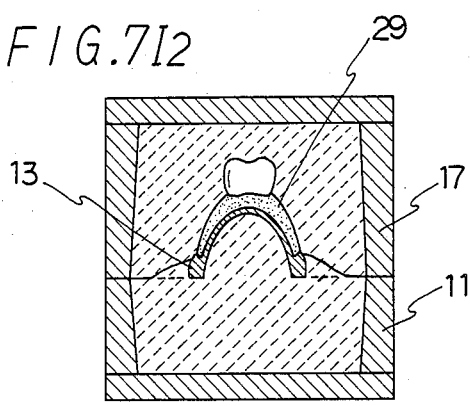
FIG.7I2
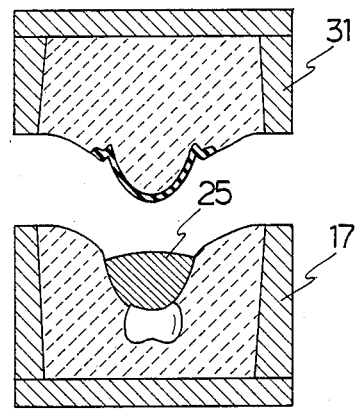
FIG.7L2
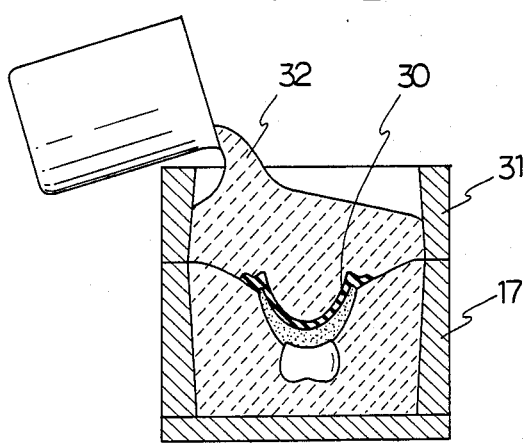
FIG.7J2

FIG.7M2
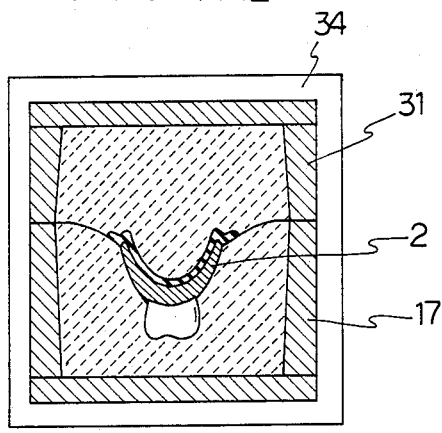
FIG.7O
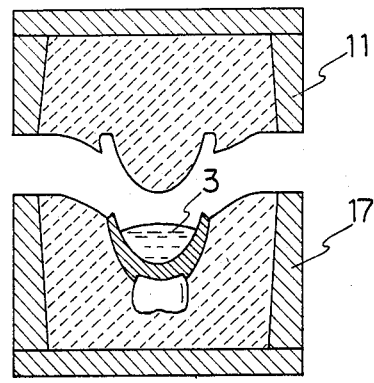
FIG.7P
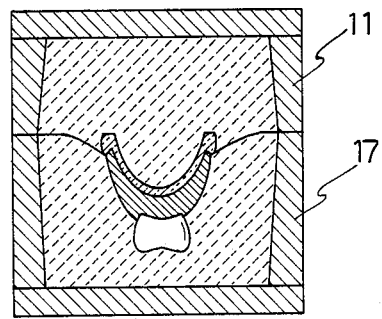
FIG.7N2
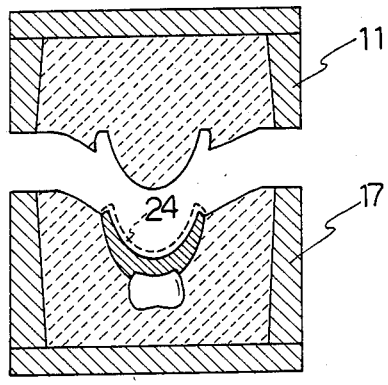
FIG.7Q
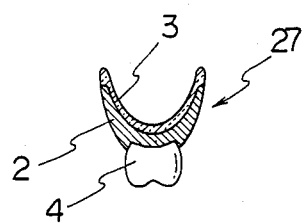

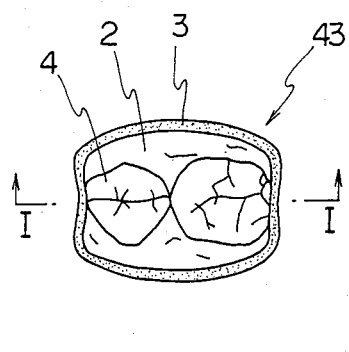
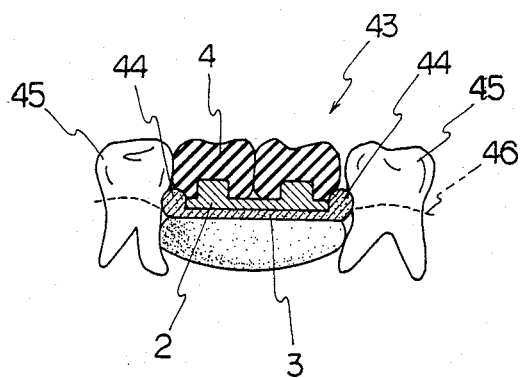
FIG.9A  FIG.9B
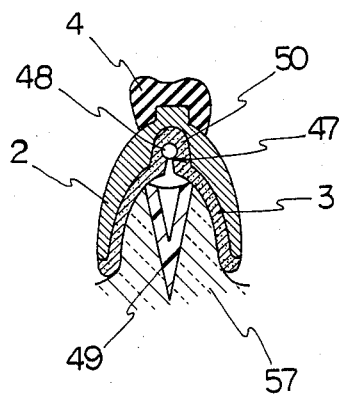
FIG.10
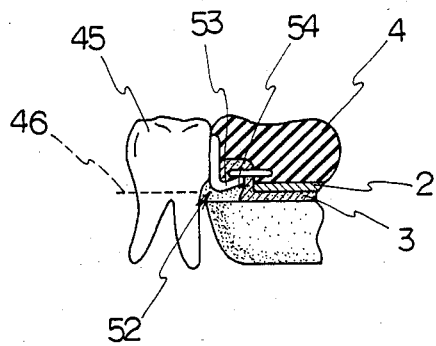
FIG.11

DENTURE BASE PROVIDED WITH RUBBER-LIKE RESILIENT LINING LAYER AND PROCESS FOR PRODUCING THE SAME

BACKGROUND OF THE INVENTION

The present invention relates to a denture base provided with a lining layer having rubber-like resilience and a process for producing the same.

It has hitherto been known that a lining layer having rubber-like resilience or flexibility is formed on the inner surface of a denture base body in order to make the support of the dental prosthesis to patient's alveolus ridge stable and strong and in order to prevent a shake, an undesirable pain and falling off at time of chewing. The materials used for the lining layer are, for instance, a mixed material of vulcanized rubber and plastic material (U.S. Pat No. 3,083,459 or U.S. Pat. No. 3,886,659), silicone rubber (U.S. Pat. No. 3,251,910 or U.S. Pat. No. 3,667,123), hydrogel (U.S. Pat No. 3,628,988 or U.S. Pat. No. 3,930,076), EVA (U.S. Pat. No. 3,727,309), a mixture of MMA polymer, MMA monomer and butyl phthalyl butylglycolate (U.S. Pat. No. 3,969,303), polyurethane (U.S. Pat. No. 4,024,636), fluorine elastomer (U.S. Pat. No. 4,251,215 or U.S. Pat. No. 4,484,894), and the like. Further, a material comprising MMA is disclosed in U.S. Pat. No. 2,457,114.

However, when the above-mentioned materials are used for a lining layer, there are some disadvantages as follows:

1. In case that a soft resin is used for a lining layer, it is unsuitable to support the attachment, since the rubber-like resilient is restricted. Further, when a pressure face is locally applied onto the lining layer and the lining layer is deformed, the lining layer cannot restore to an original form like a rubber.

2. In case that a lining layer which is a thin sheet is attached and pressed onto the inner surface of a denture base, it is difficult to fill the undercut portion which is inclined toward the alveolus ridges of a natural tooth with the lining layer and the lining layer is not sufficiently supported by natural teeth.

3. Since rubbers such as silicone rubbers are valcanized, it is difficult to process these rubbers after the formation of a lining layer.

The present invention is directed to eliminate the above-mentioned disadvantages. That is to say, a main object of the present invention is to provide a denture base having a lining layer which can be easily formed and processed by conducting a novel thermoplastic elastomer as a material used for the lining layer without any special apparatus.

SUMMARY OF THE INVENTION

According to the present invention, there is provided a denture base comprising a body having an inner surface to be in contact with patient's alveolus ridge; a lining layer covering the inner surface of the body; and an adhesive agent for bonding the lining layer to the inner surface of the body; wherein the body is made of polymethyl methacrylate; the lining layer is made of a rubber-like resilient material comprising an olefin thermoplastic elastomer or a mixed material comprising the olefin thermoplastic elastomer and a thermoplastic elastomer comprising a styrene-ethylene-butylene copolymer (hereinafter referred to as "SEBS" thermoplatic elastomer); and the adhesive agent contains a copolymer comprising an olefin and methyl methacrylate.

Further, according to the present invention, there is provided a process for producing a denture base, comprising: a step for heating and softening a material comprising an olefin thermoplastic elastomer or a mixed material comprising an olefin thermoplastic elastomer and SEBS thermoplastic elastomer to give a lining layer having a predetermined form; a step for putting the lining layer on a jaw model; a step for coating and drying an adhesive agent on the lining layer; the adhesive agent being prepared by dissolving a copolymer comprising an olefin and methyl methacrylate in a solvent; and a step for putting a rice-cake like material prepared by mixing and kneading the powder of polymethyl methacrylate into liquid methyl methacrylate monomer; and for pressing and heating the rice cake-like material subjecting to be polymerized and hardened.

Further, according to the present invention, there is provided a process for producing a denture base, comprising: a step for forming a body of a denture base having a predetermined form by polymerizing and hardening a polymethyl methacrylate resin; a step for coating and drying an adhesive agent on a body's inner surface to be in contact with a patient's alveolus ridge; the adhesive agent being prepared by dissolving a copolymer comprising an olefin and methyl methacrylate into a solvent; and a step for pressing and bonding a heated and softened lining layer on the surface coated by adhesive agent; the lining layer being made of olefin thermoplastic elastomer or a mixture of the olefin thermoplastic elastomer and SEBS thermoplastic elastomer.

BRIEF DESCRIPTION OF THE DRAWINGS

FIGS. 6A to 6N1 are schematic sectional views showing embodiments of the process of the present invention in regular order steps thereof;

FIGS. 7H2 to 7Q are shcematic sectional views showing embodiments of the process of the present invention in regular order steps thereof;

FIG. 9A is a plan view showing an example of a partial dental prosthesis which is produced by the process of the present invention.

FIG. 9B is a sectional view on lines I—I in FIG. 9A;

FIG. 10 is a sectional view showing another example of a partial dental prosthesis which is produced by the process of the present invention; and FIG. 11 is a sectional view showing another example of a partial dental prosthesis which is produced by the process of the present invention.

Figure 1:
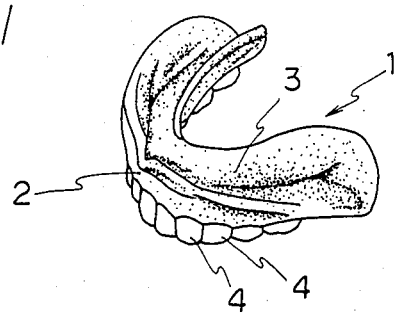
FIG. 1 is a perspective view showing an embodiment of a denture base of the present invention.

DETAILED DESCRIPTION OF THE INVENTION (a) Full denture:

FIG. 1 shows an embodiment of a denture base which is applied to a full denture of a mandible 1. In FIG. 1, numeral 2 shows a denture base body which is made of PMMA resin; numeral 3 shows a lining layer having rubber elasticity, and numeral 4 shows an artificial tooth secured to the denture base body 2. The lining layer 3 is fixed on the inner surface of the denture base body. The inner surface of denture base body means in the specification a portion of the surface of the body 1, which is adapted in order to be contacted with patient's alveolus ridge. The lining layer 3 is approximately 0.5 to 1.5 mm in thickness. The following materials can be employed in the materials of the lining layer 3 and the adhesive agents.

(b) Lining layer:

A material used for the lining layer 3 are an olefin thermoplastic elastomer including at least polyethylene or polypropylene or a mixed material of the above-mentioned olefin thermoplastic elastomer and SEBS thermoplastic elastomer. Examples of olefin thermoplastic elastomer are a hard segment comprising polyethylene or polypropylene, a soft segment comprising a homopolymer or copolymer such as butene, propylene or butadiene, or a material comprising a soft segment as a main component, the soft segment comprises a copolymer of ethylene and propylene. The above-mentioned materials have a softening point of at highetst 100° C. and a wide range of JIS A-hardness i.e. approximate 20 to 90 in JIS-hardness (hardness in Japanese Industrial Standard, and hereinafter referred to as "hardness"). TAFMER (registered trademark of Mitsui Petrochemical Industries, Ltd.) is suitably used for the olefin thermoplastic elastomers. The former is marketed as TAFMER (registered trademark) A and the latter is marketed as TAFMER (registered trademark) P.

Examples of the above mentioned TAFMER A which is α-olefin thermoplastic elastomer are a material containing either polyethylene or polypropylene as a hard segment and a material containing both polyethylene and polypropylene.

The above-mentioned olefin thermoplastic elastomer comes to be soft at the temperature of about 70° C. However, when a thermoplastic elastomer comprising a SEBS copolymer is mixed into the olefin thermoplastic elastomer, the temperature characteristic can be improved. Further, since the shape-stability, that is, shape-stability when the temperature of the elastomer is changed, of the SEBS thermoplastic elastomer is better than that of the olefin thermoplastic elastomer, the heat resistance can be improved by mixing these two materials. The SEBS thermoplastic elastomer can be obtained by hydrogenizing a stylene-butadien thermoplastic elastomer such as RABALON (registered trademark of Mitsubishi Petrochemical Company, Ltd.)

Figure 2A:
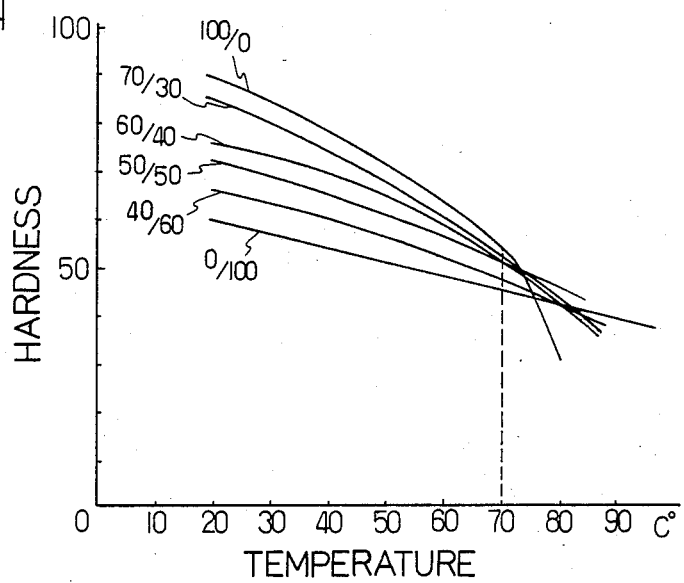
FIG. 2A is a hardness-temeprature graph when the mixing ratio of the olefin thermoplastic elastomer and SEBS thermoplastic elastomer is changed.

FIG. 2A shows a hardness-temperature characteristic curve when the mixing ratio of the olefin thermoplastic elastomer and the SEBS thermoplastic elastomer is changed.

In FIG. 2A, the numerator indicates a percentage of the olefin thermoplastic elastomer and the denominator indicates a percentage of SEBS thermoplastic elastomer.

It can be obviously understood from FIG. 2 that when the mixing ratio of SEBS thermoplastic elastomer is inceased, the softening of the mixed elastomer is repressed at the temperature of upper to about 70° C.

Further, when the hardness of SEBS thermoplastic elastomer differs from that of olefin thermoplastic elastomer, the hardness of the mixed elastomer can be adjusted by preparing the mixing ratio of SEBS thermoplastic elastomer and olefin thermoplastic elastomer. However, the percentage of the SEBS thermoplastic elastomer practically should be not less than about 75, since the adhesive strength of the mixed elastomer is lowered when the percentage of SEBS thermoplastic elastomer is more than about 75.

When employing the olefin thermoplastic elastomer solely instead of the mixed elastomer, the lining layer comes to be soft rapidly from the temperature of about 70° C. However, since the most portions of the lining layer is situated between the denture base body and the surface of the alveolus ridge and the lining layer is intercepted from the outer, the lining layer is not heated up to about 70° C. Although there is a possibility that the temperature of the peripheral portion of the lining layer is heated to the above mentioned temperature in a moment, the time to be heated is not long enough to soften the lining layer and therefore, practically the olefin thermoplastic elastomer can be solely employed.

In case that the olefin thermoplastic elastomer is used solely for the material of the lining layer, the hardness can be adjusted by mixing TAFMER A and TAFMER P.

Figure 2B:
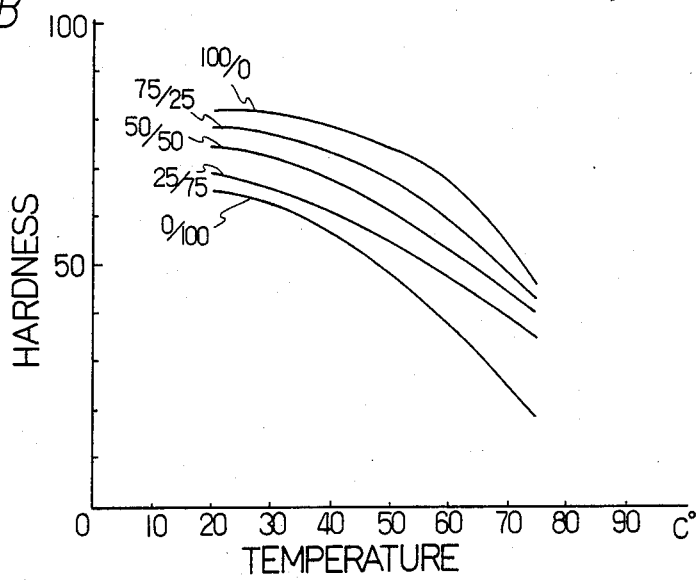
FIG. 2B is a hardness-temperature graph when the mixing ratio of two kinds of materials, both of which belong to olefin thermoplastic elastomers, is changed.

FIG. 2B shows a hardness-temeprature characteristic curve obtained by changing the mixing ratio of TAFMER A and TAFMER P. In FIG. 2B, the numerator shows the percentage of TAFMER A4085 (type number) and the denominator shows a percentage of TAFMER P680 (type number). Though the TAFMER A is excellent in compressive strength, it is too hard when it is used solely. Therefore, the hardness is suitably adjusted by mixing TAFMER P which is soft. For example, when the mixing ratio of TAFMER A to TAFMER P is 1 to 1, the hardness becomes about 70 at the temperature of 37° C.

When the molding temperature of the lining layer 3 is not less than 70° C., the lining layer can be formed. Therefore, it can be heated by means of applying an irradiation in hot water, vapor, higher alcohol, edible oil or by means of applying an electric oven.

Especially, when edible oil which can be heated up to about 200° C. is applied, the lining layer 3 can be heated to the temperature, and the liquidity of lining layer is furthermore improved. Therefore, the lining layer 3 which is inserted into a tube, or the like can be suitably heated.

In addition, it is preferable that the lining layer comprises at least two kinds of materials, that is, a hard material having a hardness of about 70 and soft material having a hardness of about 50.

Hereinafter, the result of a test with respect to the safety or the like of the material of the lining layer 3 of the above-mentioned embodiment will be described. In the test, two kinds of samples M1 and M2 are prepared as lining layers of example 1 and example 2 respectively, and the test is performed under the actual using conditions, i.e. under the condition wherein they are fixed to a PMMA-denture body made of GC Acron (registered trademark of G-C Dental Industrial Corp.) with an adhesive agent which is described later.

The sample M1 is a mixed material of TAFMER A4085 and RABALON (registered trademark) MJ6300

(type number) in a mixing ratio of 1 to 1. The sample M2 is a mixed material of TAFMER A4085 and TAFMER P680 in a mixing ratio of 1 to 1.

Safety test (i) Cutaneous primary stimulation test

Each eluent of samples M1 and M2 was applied to rabbit skin and a stimulation was examined according to Draize standard. As the result, any stimulation was not induced in the skin by the application of the eluent of samples M1 and M2, which showed negative cutaneous stimulation.

(ii) Acute toxicity test

Employing six week SD rats of both sexes, acute toxicity test was carried out by observing the animals for 14 days after one oral administration of the eluent of samples M1 and M2. As the result, no death was observed in both sexes by 50 ml/kg administration, which was almost a maximum dose which can be administered, and also any change or abnormality was not observed in a general condition and body weight of the animal with the passage of time and autopsy.

(iii) Extraction test

Extractants were extracted from the samples M1 and M2 by means of incubation with distilled water of 70° C., and they were analized through extinction degree in ultraviolet absorption spectrum 220 nm.

The extractant quantity of the sample M1 is slightly higher than that of Silastic (registered trademark of Dow Corning Co.) which is a lining layer made of silicone rubber, Tygon (registered trademark of Norton Plastic Synthetics Co., Ltd.) which is a lining layer made of polyvinyl chloride and GC Acron which is PMMA resin for a denture base. However, it is estimated that eluent of the sample M1 is within a range that gives no influence to a living body.

The extractant quantity of the sample M2 is extremely smaller than that of "Kurepeet" (registered trademark of Kureha Chemical Industry Co., Ltd) which is a lining layer made of fluorine resin, or that of "MOLLOPLAST" (registered trademark of Molloplast KG Köstner & Co. Ltd.) which is a lining layer made of silicone-rubber. Further, it can be observed that when the sample M2, except for the lining layer is solely applied, the eluent is little.

(iv) Hemolysis test

Hemolysis test was carried out on sample M1. Percent hemolysis by sample M1 after 24 and 48 hours was almost equivalent to that by Tygon (registered trademark) and was lower than that by GC Acron (registered trademark). The degree of hemoglobin denaturation by sample M1 after 24 and 48 hours was almost equivalent to that by GC Acron (registered trademark).

Both percent hemolysis and a degree of hemoglobin denaturation by sample M2 after 24 and 48 hours were almost equivalent to those by GC Acron (registered trademark), Silastic (registered trademark) and Tygon (registered trademark). Especially, percent hemolysis of the sample M2 alone, i.e. not containing the denture base body, was zero and was a minimum value among the samples as compared.

(v) Cytotoxicity and living body compatibility test

Cytotoxicity and living body compatibility were tested on samples M1 and M2 using cells of Hela S3 and Flow 7000.

The result showed that sample M1 did not have toxicity against Flow 7000 but had a low toxicity against Hela cell; i.e. in cytotoxicity test growth rate of the cells added with 400 mg/20 ml of an extract of sample M1 was 75% as compared with the control group, while in cell multiplication test on sample M1 for seven days, the growth rate of the cells was 65% as compared with the control group, both tests showing a low toxicity of sample M1. However, since a sensitivity is generally higher in a cell culture method than in an animal experiment, a toxicity to some degrees in a cell culture usually results in almost no toxicity in an animal experiment if a macromolecule compound in the test material does not decompose in a living body or does not have an electric charge. Thus, sample M1 is assumed to have almost no toxicity in the animal experiment since it had only a low toxicity in the cell culture method.

Similarly, the above tests employing cells of Hela S3 and Flow 7000 were carried out on sample M2 and the results of both tests showed almost no toxicity of the sample M2.

Property test (i) Wettability

In order to examine wettability of the samples M1 and M2 to saliva, contact angle of the samples to water were measured by means of a contact-angle precision measurement instrument CA-1 produced by Kyowa Scientific Equipment Co. Ltd.

TABLE 1

| | Samples for elastic lining layer | | Contact angle |
|---|---|---|---|
| Ex. No. | | | |
| 2 | sample M2 | | 91 |
| Ref. Ex. 1 | Molloplast | (registered trademark) | 98 |
| Ref. Ex. 2 | Neosnugger | (registered trademark) | 106 |
| Ref. Ex. 3 | Kurepeet | (registered trademark) | 83 |

The data in Table 1 were obtained after subjecting the samples to dipping into distilled water of 50° C. for 24 hours and then subjecting the surfaces of the samples to drying.

As shown in Table 1, it can be obviously understood that the contact angle of the sample M1 is more excellent than that of a lining layer made of silicone such as Molloplast (registered trademark) or Neosnugger (registered trademark), each of them are made by Neo Dental Chemical Products CO., LTD.

(ii) Discoloration test

The color of the lining layer has a possibility to be shaded by foods when the dental prosthesis is applied into a mouth. From the viewpoint of keeping the beauty of the lining layer, it is preferable that the lining layer is not shaded. Therefore, we examined the discoloration test of the lining layer by using turmeric solution which was seemed to have been a main factor of discoloration. Marketed lining layers were used as comparative samples.

Conditions of the test: Samples were dipped in 1.0 g/l of turmeric solution whose temperature was 37° C. for 24 hours, and then they were washed with water. The $\Delta^*Eab$ valueis in CIE 1976 color specification of the samples were measured with a color-difference meter CR-100 which is made by Minolta Camera Co., Ltd.

TABLE 2

| Samples | $\Delta^*Eab$ |
|---|---|
| Ex. No. | |

TABLE 2-continued

| | Samples | | $\Delta^*Eab$ |
|---|---|---|---|
| 1 | | M1 | 7.8 |
| 2 | | M2 | 5.6 |
| Ref. Ex. 3 | Kurepeet | (registered trademark) | 5.1 |
| Ref. Ex. 2 | Neosnugger | (registered trademark) | 27.7 |
| Ref. Ex. 1 | Molloplast | (registered trademark) | 12.4 |
| Ref. Ex. 4 | Super Soft | (registered trademark) | 40.0 |

As is shown in Table 2, it can be understood that the degree of discoloration of the sample M1 and M2 are smaller than that of Neosnugger, Molloplast, or acrylic lining layer made of Super Soft (registered trademark of Coe Laboratory Inc.)

(iii) Stress relaxation

In order to evaluate the degree of parmanent deformation of the lining layer and the safety for water as an elastomer in a mouth, the stress relaxation in water of 50° C. was measured. The elongation ratio was measured in a linear region of viscoelasticity, and the obtained data were analized in accordance with the change on standing of relative stress. The following Table 3 shows a rate constant of the stress-relaxation K at the temperature of 50° C. in water.

TABLE 3

| | Samples | K ($\times 10^{-7}$/sec) |
|---|---|---|
| Ex. No. | | |
| 1 | M1 | 0.5 |
| 2 | M2 | 0.6 |
| Ref. Ex. 1 | Molloplast | 3.6 |
| Ref. Ex. 3 | Kurepeet | 33.0 |
| Ref. Ex. 2 | Neosnugger | 120.0 |

As a result of Table 3, it can be understood that the change of the rubber-resilient factors of M1 and M2 are small, and the flow-deformaton and change of the molecular structure have a difficulty to be changed.

(iv) Elastic coefficiency

Elastic coefficiency (Young's modulus) which shows the softness of the lining layer in a mouth was measured.

TABLE 4

| | Samples | Young's modulus (dyn/cm$^2$) |
|---|---|---|
| Ex. No. | | |
| 1 | M1 | $(1.8 \pm 0.2) \times 10^8$ |
| 2 | M2 | $(1.0 \pm 0.2) \times 10^8$ |
| Ref. Ex. 3 | Kurepeet | $(7.4 \pm 0.2) \times 10^8$ |
| Ref. Ex. 1 | Molloplast | $(1.9 \pm 0.2) \times 10^7$ |
| Ref. Ex. 2 | Neosnugger | $(1.6 \pm 0.2) \times 10^7$ |

The kurepeet was too hard for use, and the Molloplast and Neosnugger were too soft for use.

(c) Adhesive agent:

The olefin thermoplastic elastomer which is used for a material of the lining layer 3 is extremely stable from a phisical and chemical viewpoint, since the lining layer 3 comprises a non-polar saturated hydrocarbon as a main component, and therefore, it is suitably used for a material of the lining layer. However, the chemical stability makes the adhesive property to the denture base which is made of a dissimilar polymeric material difficult. The above-mentioned problem has not been solved yet in the industrial field of polymer chemistry.

The adhesive agent in the present invention is applied in order to eliminate the above-mentioned problem. That is to say, the adhesive agent in the present invention which is used for fixing a lining layer 3 to a denture base body 2 made of PMMA, comprises a copolymer of polyethylene and MMA.

(i) Process for producing an adhesive agent

Polyethylene was subjected to dissolving in toluene by heating in a polymerization reactor. A predetermined quantity of MMA and benzoyl peroxide (hereinafter referred to as "BPO") as a radical polymerization initiator were added into the polymerization reactor and then they were subjected to graft copolymerization in nitrogen gas at the temperature of 70° C.

The graft copolymerization was carried for 4 hours and then the polymerized solution was added into a large amount of bad solvent such as methanol in the instant example to give a polymer by precipitating and separating the polymer. The separation of PMMA and MMA monomer was carried out with Ethyl acetate in a soxhlet's extractor. After the extraction of 8 hours, PMMA and MMA were dissolved and removed. When analysing the obtained copolymer by means of infrared spectroanalysis, or the like, it was confirmed that a adhesvie agent having an objective molecular structure was obtained.

The degree of polymerization, the degree of graft and the effciciency of graft of three kinds of polyethylene-MMA graft copolymerization products A, B and C that were obtaind by changing the concentration of BPO are shown in Table 5.

TABLE 5

| Products | Concentration of BPO | Degree of polymerization of MMA (%) | Degree of graft (%) | Efficiency of graft (%) |
|---|---|---|---|---|
| A | 40 | 42.7 | 7.3 | 17.2 |
| B | 50 | 43.0 | 8.7 | 24.3 |
| C | 60 | 40.2 | 10.8 | 27.0 |

In Table 5, the unit of BPO concentration is $\times 10^{-3}$ mol/l. The degree of graft and the efficiency of graft were obtaind by calcurating in accordance with the following equations.

$$\text{Degree of graft (\%)} = \frac{\text{Amount of grafted monomers}}{\text{Amount of main chain polymer}} \times 100$$

$$\text{Efficiency of graft (\%)} = \frac{\text{Amount of grafted monomers}}{\text{Amount of polymerized monomers}} \times 100$$

The obtained graft copolymer was subjected to dissolving in 1,1,1-trichloroethane, and a liquid adhesive agent was obtained. The 1,1,1-trichloroethane was preferably used as the above mentioned solvent, since 1,1,1-trichloroethane had no toxicity, and could be easily evaporated, which was derived from that the 1,1,1-trichloroethane had a boiling point of 74.1° C.

Examples of a solvent used for the adhesive agent are organic chloride solvents, toluene, xylene, ethers, and the like.

Figure 3:
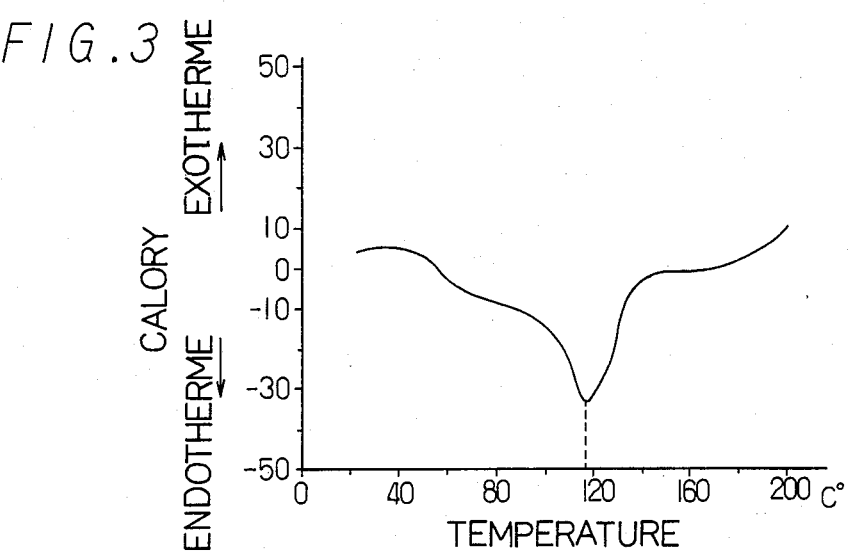
FIG. 3 is a characteristic graph showing the results of thermal properties of the copolymer products by means of differential thermal analysis.

FIG. 3 shows an analysis result of copolymerization product by means of a differential thermal analysis meter. As shown in FIG. 3, it was measured that the melting point of the copolymerization product B was 118° C. The result shows that the copolymerization product is melted when an adhesive agent comprising the copolymerization product B is applied on a lining layer and then rice-cake like PMMA is pressed at the temperature of about 100° to 130° C. to give a polymerized product.

Therefore, it can be estimated that the adhesive function yields and the function can be improved. Indeed, it was confirmed that the adhesive function yielded at the temperature of about 100° C. by the relaxation phenomenon when adhesive time was sufficient.

(ii) Adhesive strength

Figure 4:
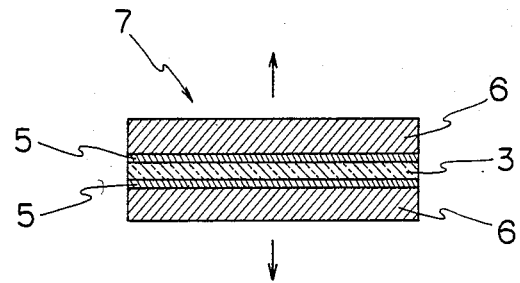
FIG. 4 is a schematic sectional view of a sample which is used for adhesive-strength-test.

As shown in FIG. 4, the adhesive agent 5,5 which was prepared by the same process as mentioned above was applied on both surfaces of the lining layer 3 whose thickness was about 0.7 mm and then the adhesive agent 5,5 was sufficiently dried.

Thereafter, rice-cake like PMMA which was prepared by mixing a powder of PMMA with liquid MMA monomer was mounted on the both surfaces of the material of lining layer 3, and they were pressed and heated in order to polymerize the PMMA. The lining layer 3 made of the sample M1 and PMMA resin plate 6,6 which was the same resin as the denture base body were adhered at the same time of forming a PMMA resin plate.

After the adhereance, the obtained material was processed into a square test piece of 10 mm × 10 mm. Sequentially, the test piece 7 was pulled by an Autograph (registered trademark of Shimazu Corporation) DSS-5000 in order to measure the adhesive strength thereof. The following Table 6 shows the measured values of the copolymerization products A, B and C which were mentioned above and the commercially available materials D and E. The material D is Molloplast and the material E is Kurepeet, and both of them were adhered in accordance with their instruction books.

TABLE 6

| A | B | C | D | E |
|---|---|---|---|---|
| 45 | 60 | 55 | 9.5 | 100 |

(unit: kg/cm$^2$)

As is shown in Table 6, in case that the above-mentioned lining layer was adhered at the same time of polymerization with the above-mentioned adhesive agent, the adhesive strength was 60 kg/cm$^2$. The adhesive strength was sufficient for actual use. In case that the same sample M2 was adhered for polymerization with the adhesive agent B by the same procedure as mentioned above, the adhesive strength was 80 kg/cm$^2$.

On the other hand, in case that after the PMMA resin plate was polymerized for curing, the adhesive agent was applied on the PMMA resin plate and the lining layer was pressed for adhesion on the adhesive agent, the adhesive strength of M1 and M2 were 41 kg/cm$^2$ and 60 kg/cm$^2$ respectively.

(d) Another adhesive agent:

As another embodiment of the adhesive agent, polypropylene was applied instead of the above mentioned polyethylene. The polypropylene was polymerized with MMA under the same conditions as mentioned above, i.e. the conditions for producing the product B, and a graft copolymer of polypropylene and MMA was produced. The graft copolymer was dissolved in a solvent comprising o-xylene to give an adhesive agent. By applying the obtained adhesive agent, the lining layer made of sample M1 and PMMA resin plate were bonded with each other. As a result of conducting the lining layer to the same tension test as mentioned above, the value of adhesive strength was 38 kg/cm$^2$. From the above-mentioned result, it appears that the practical adhesive strength can be obtained when the copolymer of polypropylene and MMA is employed as a material of adhesive agent.

Further, the above-mentioned TAFMER A4085 which was α-olefin thermoplastic elastomer was used as a main chain polymer. That is to say, the TAFMER A4085 was graft polymerized with MMA under the same conditions as mentioned above, i.e. the conditions for producing the product B, and then a copolymer comprising α-olefin thermoplastic elastomer and MMA was obtained. The obtained copolymer was dissolved in a solvent comprising o-xylene to give an adhesive agent. The lining layer made of the sample M1 and the PMMA resin plate were bonded with each other, and then the above-mentioned tension test was carried out. As a result of that, the adhesive strength was 50 kg/cm$^2$. The strength was sufficient for practical using.

The reason why the copolymer comprising an olefin and MMA such as a graft copolymer comprising polyethylene and MMA, or a graft copolymer comprising polypropylene and MMA or a copolymer comprising an α-olefin thermoplastic elastomer and MMA is used in the adhesive agent is that the copolymer comprising an olefin and MMA shows a compatibility with polyethylene or polypropylene which is contained in the olefin thermoplastic elastomer. Therefore, not only the above-mentioned copolymer but also a ternary polymer comprising polyethylene, polypropylene and MMA or a ternary polymer prepared by copolymerizing a copolymer comprising polyethylene or polypropylene and other material such as vinyl acetate or MMA.

Figure 5:
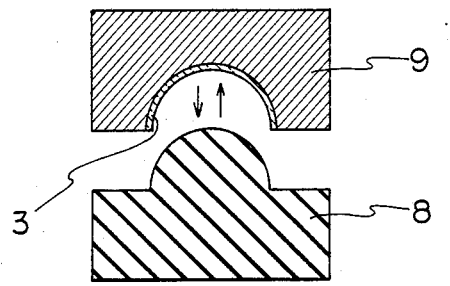
FIG. 5 is a schematic sectional view showing a device which is used for the life test.

(e) Endurance of lining layer and adhesive agent:

In FIG. 5 showing an endurance test device, numeral 8 denotes a base made of stainless steel which has a semi-cylindrical projection having 10 mm radius. Numeral 9 denotes a PMMA resin plate or board made of GC Acron. The plate 9 is provided with a semi-cylindrical recessed portion having 10 mm radius. A lining layer 3 having a thickness of 1 mm which is made of the sample M1 or M2 is bonded on the inner surface of the recessed portion by means of the above mentioned adhesive agent (hereinafter referred to product B).

By using the above-mentioned test device, an alternating load of 3 Hz and 50 kg was applied in the direction of the Arrow shown in FIG. 5 by means of a hydraulic serbo dynamic responce testing machine which is made by Saginomiya seisakusho Inc., and the degree of fatigue of adhereance was observed. The following Table 7 shows a result of the measurement.

TABLE 7

| | Material | 54,000 times | 140,000 times |
|---|---|---|---|
| Ex. No. | | | |
| 1 | M1 | No deformation due to fatigue | No deformation due to fatigue |
| 2 | M2 | Small cracks occurred at the boundary surface. No changes of hardness | Cracks occurred. No changes of hardness |
| Ref. Ex.3 | Kurepeet | Large deformation occurred due to fatigue. Many cracks at the boundary surface occurred | Further large deformation occurred due to fatigue. Cracks occurred. |
| Ref. | Molloplast B | Hardened | Hardened |

TABLE 7-continued

| | Material | 54,000 times | 140,000 times |
|---|---|---|---|
| Ex. 1 | | Partially exfoliation occurred. | Exfoliation occurred No changes of hardness No deformation |
| Ref. Ex.2 | Neosnugger | Partially exfoliation occuured. | Exfoliation occurred. No changes of hardness Deformation occurred. |

As is shown in Table 7, it is confirmed that when the lining layer and the adhesive agent which are made of the above-mentioned materials used in the embodiments, they are superior in endurance to the commercially available materials.

(f) Process for producing a denture base:

(i) Method of adhesion at the same time of polymerization

Figure 6A:
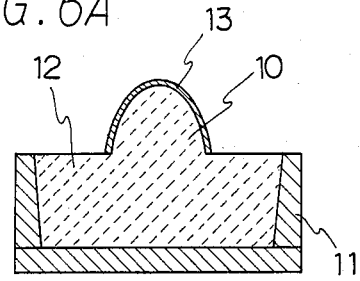
Figure 6E:
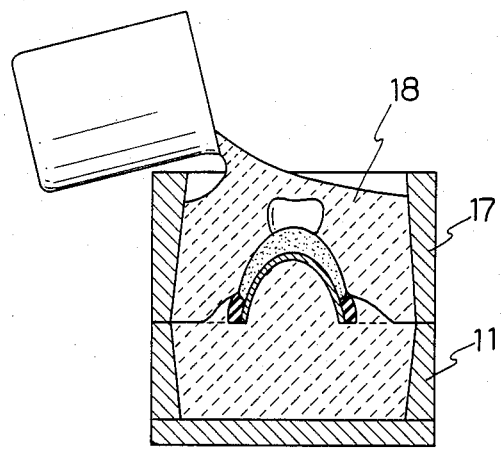
Figure 6B:
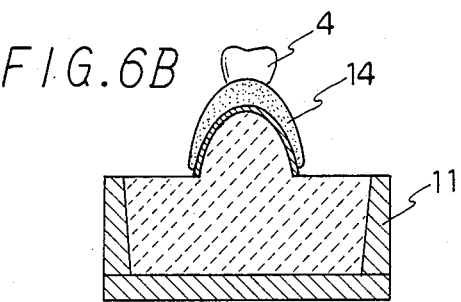
Figure 6F:
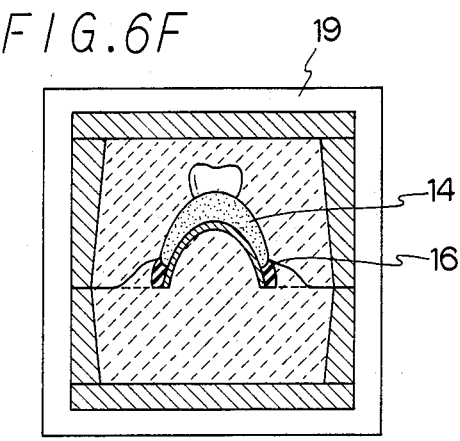
Figure 6C:
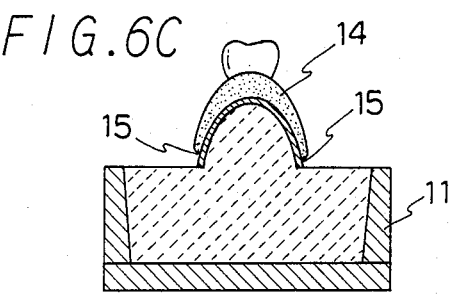
Figure 6G:
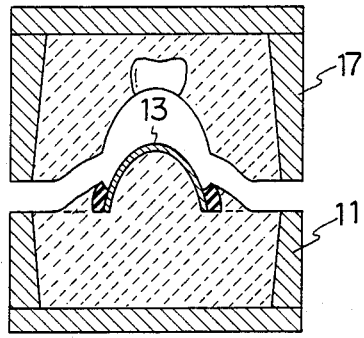
Figure 6D:
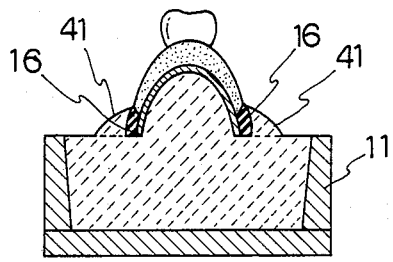

FIG. 6A to FIG. 6H1 respectively shows an embodiment of the process for producing a denture base in which a lining layer and an adhesive agent are used in the present invention, and the lining layer is bonded at the same time that the denture base is subjected to polymerization. Hereinafter, the process for producing the lining layer will be explained in accordance with FIG. 6A to FIG. 6H1.

FIG. 6A

At first, a jaw model 10 of which form is printed from the patient's jaw is prepared by means of plaster 12 at the inner space of the first flask 11. A thermosetting plastic material such as plastic clay, photo-polimerizable resin or two components resin having a predetermined thickness, for example, about 1 mm is mounted as a spacer 13 on the portion of the jaw model 10 to which a lining layer should be provided. The spacer 13 is a substitutive material for a lining layer which will be formed in the later step. Therefore, in order to obtain a suitable form as a lining layer, the spacer 13 can be deformed in the step. For example, portions of the spacer 13 to be in contact with the thin portions of gingiva of the patient should be thickened. The spacer 13 is formed when it is in a plastic state, and then is subjected to hardening.

FIG. 6B

The wax 14 is mounted on the jaw model 10 provided with the spacer 13 in order to design a form of denture base, and artificial teeth 4 are arranged on the wax 14. Such processes are usually treated by dentists.

FIG. 6C

Peripheral portions of the provisional denture base body made of the wax 14 are resected to form a lining layer having a prescribed width. The portions 15, 15 to be resected are determined with due regard to whether the portion should be formed as a part of the lining layer, or a denture base body since the portions 15, 15 to be resected will be formed as a part of the lining layer in the later step.

FIG. 6D

Unvulcanized plastic rubbers 16, 16 are filled in the resected portions 15, 15 of the wax 14. The unvulcanized rubber 16, 16 is formed to be relatively thick in order to make the border line of the denture base body and the lining layer obvious. Therefore, the unvulcanized rubber will be vulcanized and hardened. Sequentially, plasters 41, 41 are poured around the vulcanized rubbers 16, 16 and the vulcanized rubbers 16, 16 are fixed. The hardenable plastic material as mentioned above can be used instead of the vulcanized rubber 16, 16. Further, the same material as that of the spacer 13, i.e. thermosetting plastic clay can be used instead of the vulcanized rubber.

FIG. 6E

After a separation agent is applied on the surface of the plaster model in the first flask 11, a second flask 17 is mounted on the first flask 11 and a plaster slurry 18 is poured into the second flask 17.

FIG. 6F

After the plaster is hardened, the first and the second flasks 11 and 17, both of which are in a conbined state, are inserted into a container 19 and then the container 19 is immersed in hot water of about 100° C. for about 5 minutes. Thus, the wax 14 is melted.

FIG. 6G

The pair of flasks 11 and 17 is separated, and the first flask 11 is washed with hot water to remove the melted wax 14.

FIG. 6H1

When the spacer 13 and the vulcanized rubber 16 are left on the jaw model, a separating agent is applied on the surface of the plaster of the flask 11, and then the third flask 20 is laid on the separating agent. Thereafter, the plaster 21 having a fluid state is filled in the third flask 20.

FIG. 6I1

After the plaster 21 is hardened, the first and the third flasks 11 and 20 are separated from each other, and the spacer 13 and the vulcanized rubber 16 are removed. The obtained space 22 corresponds to a space for forming a lining layer. A material for the lining layer 3 is filled in the space 22 in the state that the material 3 is heated to be melted. Numeral 23, 23 denotes a groove for burr. The material for lining layer 3 can be heated by immersing into hot water, higher alcohol, or edible oil, and it can be formed at the temperature of about 100° C.

FIG. 6J1

The first and third flasks 11 and 20 are securely tightened, and the lining layer 3 is formed.

FIG. 6K1

After the cooling of the melted lining layer 3, the first and third flasks 11 and 20 are separated to give a lining layer 3 mounted on the jaw model 10 of the first flask 11. An adhesive agent 24 is applied on the surface of the lining layer 3.

FIG. 6L1

After the adhesive agent is dried, rice-cake like PMMA25 is filled in the space between the first and second flasks 11 and 17 which is the space for forming a denture base body.

FIG. 6M1

Consequently, the first and second flasks 11 and 17 are securely tightened each other, are laid in the container 26, and are heated by hot water or vapour having a temperature of about 100° to 130° C. subjecting PMMA to the polymerization for curing. At the same time, the lining layer 3 is adhered with the denture base body 2.

FIG. 6N1

After the polymerization, the first and second flask 11 and 17 are separated from each other, the plaster is broken, and the dental prosthesis is taken out. Consequently, thick portions of the lining layer is grindformed, the surface of the body 2 of the denture base is polished, and a process for producing of a denture prosthesis in the present invention is completed.

(ii) Method of adhesion after polymerization (Method of heating adhesion)

FIG. 7H2 to FIG. 7Q show another process for producing a denture base in their steps' order, wherein a linig layer and an adhesive agent according to the present invention are used, and after the denture base is polymerized, the lining layer is heated to be softened and melted, and is bonded on the surface of the denture base.

Figures of Steps correspondig to FIG. 6A to FIG. 6G are eliminated, since they are the same processes as are shown in FIG. 6A to FIG. 6G. Hereinafter, the later steps of the step 6G will be explained.

FIG. 7H2

Flexible parting films 28, 28 such as polyethylene films, are arranged on the surfaces of the plaster models. A plastic material 29, e.g. clay, is filled into a space for forming a denture base between the two films 28, 28. The plastic material 29 is a material to give a form-supportability that the form can be possessed for at least a certain time after the forming.

FIG. 7I2

The flasks 11 and 17 are tightened with each other, and the above-mentioned plastic material 29 is formed in accordance with the form of the body of the denture base.

FIG. 7J2

In the state that the flask 11 and 17 are separated and the formed plastic material 29 is mounted on the flask 17, the flask 17 is turned up to down. Thereafter, a two-components silicone rubber is mixed and coated on the surface of the plastic material 29 and is hardened to be formed a rubber layer 30 having a thickness of about 1 to 2 mm. Consequently, another flask 31 is put on the flask 17, and the plaster slurry 32 is poured into the flask 31. The rubber layer 30 is used as a die for the denture base body when the denture base body is formed. Therefore, even if there exists undercut portion in the body of the dentue base, the rubber layer 30 can be easily taken out due to the elasticity thereof.

FIG. 7K2

After the plaster 32 is hardened, the flasks 17 and 31 are separated from each other, and the plastic material 29 is removed with the parting films 28, 28.

FIG. 7L2

A rice-cake like PMMA which is prepared by adding a polymerization initiator into liquid MMA monomer and mixing a powder of PMMA is filled into the space for forming the denture base body.

FIG. 7M2

Flasks 17 and 31 are tightened with each other and are inserted into a container 34 subjecting to heating at the temperture of about 100° to 130° C. in vapour. The rice-cake like PMMA is polymerized, and the denture base body 2 is formed.

FIG. 7N2

The flasks 17 and 31 are separated from each other. An adhesive agent 24 is coated on the exposed surface of the denture base body 2, and is dried thereafter. A spacer 13 is removed from a flask 11 in the step shown in FIG. 6I2.

FIG. 7O

A lining layer is heated and softened at the temperature of about 120° C. and is filled into the recessed portion of the denture base body 2. It is necessary that the range of the temperature for heating contains both the forming temperature of the lining layer 3 and the softening temperature of the adhesive agent 24.

FIG. 7P

Therefore, the flasks 11 and 17 are tightened with each other. The compression molding method or injection molding method can be employed for filling the linig layer 3 into the flask 17.

However, since the lining layer 3 can be formed at the temperature of about 120° C., it can be heated to be formed in hot water, vapor or edible oil. Therefore, there is no necessity to use a special press-forming device or injection molding device.

FIG. 7Q

After the flasks 11 and 17 are cooled, they are separated from each other and a dental prosthesis 27 is taken out from the flasks 11 and 17 by breaking the plaster. Then the lining layer is readjusted by grinding, or the like. Further, after the body 2 of the denture base is polished, the dental prosthesis 27 is completed.

In the above-mentioned process, when there is no undercut portion in the jaw model 10, the steps of FIG. 7H2 and FIG. 7J2 can be omitted. In that case, the spacer 13 is left in the plaster model on the flask 11 at the step corresponding to FIG. 6G so that the spacer 13 can be used as a die for molding a denture base body.

Hereinafter, different points between the above adhesion for polymerization method and the adhesion after polymerization method are explained. In the method of adhesion at the same time of polymerization, there is an advantage that the adhesive strength between the denture base body and the lining layer is very high. However, there is a disadvantage that the air bubbles generate on the adhesive surface of the lining layer due to a pressure-drop, since when rice-cake like PMMA generally expands immediately after the polymerization, and after that, contrarily, it gradually contracts with the progress of the polymerization.

On the other hand, the method of adhesion after polymerization has an advantage that there is no fear for generation of bubbles and the finished result is beautiful though in the method, adhesive strength is a little lower, however, there is no problem in practical use, than that of the method of adhesion at the same time of polymerization.

(iii) Method for adhering a lining layer to an old dental prosthesis

Generally, a dental prosthesis comes to be unmatched to the corresponding alveolus ridge during the use for several years. Therefore, the denture base must be reformed per every several years.

FIG. 8A to FIG. 8F show a process for bonding the lining layer in their step-order when the denture base is reformed as mentioned above. The method is an example of an practical application of the above method of adhesion for polymerization.

FIG. 8A

An impression material 35 made of a silicone impression material or an algenate impression material is filled in the inner surface of the denture base body 2.

FIG. 8B

Figure 8A:
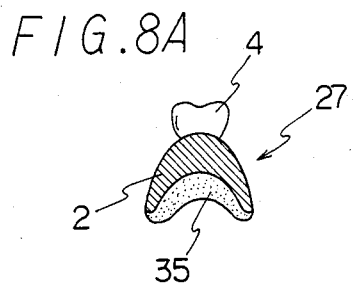
FIGS. 8A to 8F are another embodiments of the process of the present invention in regular order steps thereof.
Figure 8B:
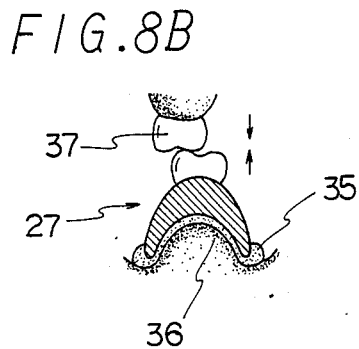
Figure 8C:
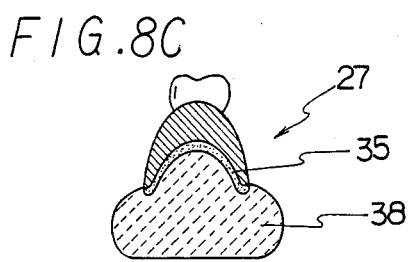
Figure 8D:
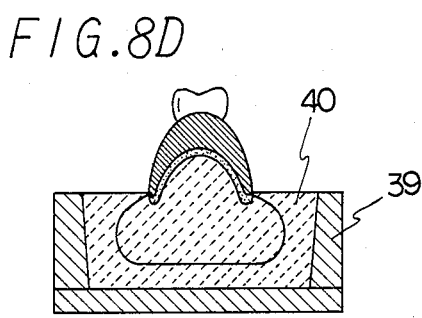
Figure 8E:
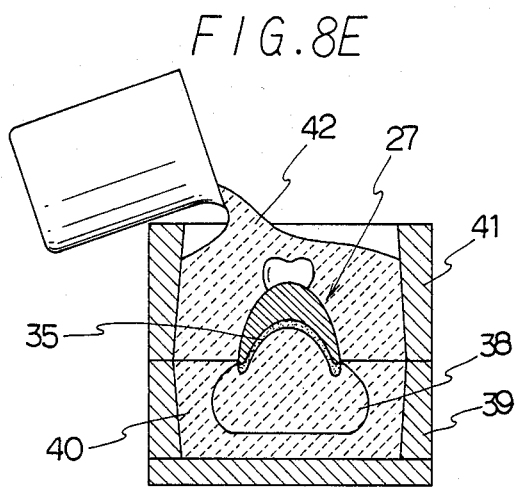
Figure 8F:
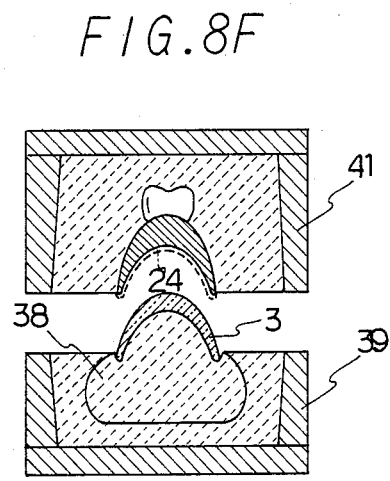

The processed dental prosthesis put on the alveolus ridge 36 in a mouth of a patient, the teeth are occluded as shown by arrows in FIG. 8B, and the impression is obtained.

FIG. 8C

After the excessive impression material is removed, the plaster slurry is poured into the inner surface of the impression material 35 and is hardened.

FIG. 8D

The above dental prosthesis 27 is put in a flask 39 with the plaster 38 is fixed by another plaster 40.

FIG. 8E

After a parting agent is coated on the surface of the hardened plaster 40, another flask 41 is put on the flask 30, and the plaster 42 is poured into the flask 41 so that the dental porsthesis is buried in the plaster 42.

FIG. 8F

After the plaster is hardened, the pair of flasks 39 and 41 is separated, and the impression material is removed. After the inner surface of the body 2 of the denture base is thinly scrapped so that a new surface comes out, an adhesive agent 24 is coated on the new surface and is dried. At the same time, a lining layer 3 which is in heat-softened or melted state is put on the surface of the jaw model of plaster 38.

Then the process sequences through the same steps as is shown in FIG. 7P and FIG. 7Q, and the linig-layer-bonding work is completed.

(g) Partial dental prosthesis and attachment:

The above-mentioned process for producing is effective when the process is applied to the production of a partial dental prosthesis or a dental prosthesis having an attachment.

FIG. 9A and FIG. 9B show a partial dental prosthesis 43. A lining layer 3 has projections 44, 44 at both ends thereof. The projections 44, 44 have a function for holding the partial dental prosthesis, since the projections are abutted to undercut portions which are inclined toward the alveolus ridges of the adjointing natural teeth 45, 45. Numeral 46 denotes an alveolus ridge. When the above-mentioned structure is formed, the projections 44, 44 can move toward the alveolus ridges, and therefore projections does not exert a wrong influence upon the stress-breaking movement of the denture.

FIG. 10 shows an example in which the denture base of the present invention is employed in a stud-attachment. In FIG. 10, numeral 10 denotes a metal stud, and numeral 3 denotes a lining layer. A female part of the attachment 47 is formed at the same time as the lining layer 3 is formed. Numeral 51 denotes a gum portion.

FIG. 11 shows an example in which the denture base of the present invention is employed in a Dalbo attachment 52. In FIG. 11, a male part 53 made of metal is fixed to a natural tooth 45. Numeral 3 denotes a lining layer, and a female part 54 for resiliently holding the male part 53 is formed integlatedly and simultaneously with the lining layer 3. The female part 54 has a metal ring 55 fixed to an artificial tooth 4 so that the metal ring 55 can receive and engage with the male part 53. The lining layer 3 is provided with two projecting portions which are projected from both lateral sides 44 of the attachment 52 to abut to the undercut portion of the natural tooth 45. The female parts 54, 54 can allow the stress-breaking movement generating from the denture toward the alveolus ridges.

According to the present invention, there can be obtained some advantages as mentioned hereinafter.

1. By employing an olefin thermoplastic elastomer or a mixed material of the olefin thermoplastic elastomer and a thermoplastic elastomer made of styrene-ethylene-butylene ternarypolymer as a lining layer, and employing an adhesive agent containing a copolymer comprising an olefin and MMA, the lining layer can be strongly bonded to a denture base body.

2. Since the lining layer is softened at the temperature about 70° C. or the more, the lining layer can be formed by heating in hot water, vapor or edible oil. Therefore, any forms of lining layer can be easily manufactured without any special apparatus.

3. Since the hardness of the lining layer can be easily adjusted, optimum hardness can be selected in accordance with the case of a disease, and a disadvantage of a conventionally available material such as too hard, too soft, or the like can be eliminated. That is to say, a lining layer having a relatively hard portion and a relatively soft portion can be used in accordance with functional characterisitics of different parts in a mouth. In that case, boader lines or faces can be completely incorporated and continuously formed.

4. Since olefin thermoplastic elastomer is employed as a linig layer, the excellent properties of an olefin, e.g. pertinent wettability for saliva, resistance against pollution or erosion due to bacilli in a mouth, anti-died-property against coloring agent in foods, and the like, are effected, and the characteristics as a lining layer are improved.

5. Since the rubber-like resilience of the lining layer does not almost parmanently change, and the lining layer can be securely bonded to the denture base body, a supporting function can hold a good and stable absorbing-force for a long time in use.

6. Since the lining layer can be freely formed without any ristriction, various kinds of female parts of attachments, e.g. not only a full or partial dental prosthesis but also in a Dalbo attachment, stad attachment, or the like, can be formed as a part of the lining layer at the same time. The supporting force of the female part of the lining layer does not decrease for a long time, since the female part resiliently supports and fixes the male part due to the rubber-like resilience thereof. On the contrary, the rubber-like resilience effects to decrease loads applied to an alveolus ridge of a patient, since the rubber-like resilient female part can absorb a shock applied to the dental prosthesis.

7. The projection comprising the same materials of the lining layer which is contacted with the undercut portions of natural teeth do not exert a wrong influence upon the movement of the denture toward the alveolus ridges. Therefore, the stress-breaking movement of the lining layer can be enoughly utilized.

8. In case the method of adhesion polymerization is employed, a lining layer is formed by means of a jaw model which is formed in the first flask, and thereafter, the denture base is polymerized for the formation under the state that the lining layer is mounted on the jaw model. Therefore, configuration, thickness, or the like of the lining layer can be freely determined, and there is no danger that errors or clearances occur between the configuration of the lining layer and that of the denture base body, and further, a completed denture base fit with a supporting surface of the alveolus ridge without any gap.

9. In case that the method of adhesion after polymerization is employed the shrink of the denture base body during curing polymerization does not exert a bad influence upon the bonding of the body and the lining layer. That is to say, there is no danger that air bubbles generate on the adhesive surface of the body, and a beautifle finish can be obtained.

What we claim is:

1. A denture base for a dental prosthesis comprising:
 (a) a body having an inner surface to be in contact with patient's alveolus ridge;

(b) a lining layer covering the inner surface of the body; and
(c) an adhesive agent for bonding the lining layer to the inner surface of the body;
wherein said body is made of polymethyl methacrylate; said lining layer is made of a rubber-like resilient material comprising an olefin thermoplastic elastomer; and said adhesive agent contains a copolymer comprising an olefin and methyl methacrylate.

2. The denture base of claim 1, wherein said rubber-like resilient material comprises a mixture of said olefin thermoplastic elastomer and a thermoplastic elastomer comprising styrene-ethylene-butylene copolymer.

3. The denture base of claim 1, wherein said olefin thermoplastic elastomer in said lining layer contains at least polyethylene or polypropylene; and said adhesive agent comprises a copolymer of polyethylene or polypropylene and methyl methacrylate.

4. The dentrue base of claim 1, wherein said olefin thermoplastic elastomer contains at least polyethylene or polypropylene; and said adhesive agent comprises a copolymer of α-olefin thermoplastic elastomer and methyl methacrylate.

5. The denture base of claim 1, wherein said lining layer has projections which can permit the stress-breaking movement generating from the denture toward the alveolus ridge to be in contact with undercut portion which are inclined toward the alveous ridges of natural tooth so that said dental prosthesis is holded by said natural tooth.

6. The denture base of claim 1, wherein said lining layer has a female part which can permit the stress-breaking movement generating from the denture toward the alveolus ridge for a stud attachment.

7. The denture base of claim 5, wherein said lining layer has a female part which can permit the stress-breaking movement generating from the denture toward the alveolus ridge for a stud attachment.

8. The denture base of claim 1, wherein said lining layer has a female part which can permit the stress-breaking movement generating from the denture toward the alveolus ridge for a Dalbo attachment.

9. The denture base of claim 5, wherein said lining layer has a female part which can permit the stress-breaking movement generating from the denture toward the alveolus ridge for a Dalbo attachment.

10. A process for producing a denture base, comprising:
(a) a step for heating and softening a material comprising an olefin thermoplastic elastomer or a mixed material comprising an olefin thermoplastic elastomer and a thermoplastic elastomer comprising a styrene-ethylene-butylene copolymer to give a lining layer having a predetermined form;
(b) a step for putting said lining layer on a jaw model;
(c) a step for coating and drying an adhesive agent on said lining layer; said adhesive agent being prepared by dissolving a copolymer comprising an olefin and methyl methacrylate in a solvent; and
(d) a step for putting a rice-cake like material prepared by mixing and kneading the powder of polymethyl methacrylate monomer into liquid methyl methacrylate; and for pressing and heating said rice-cake like material subjecting to be copolymerized and hardened.

11. A process for producing a denture base, comprising:
(a) a step for forming a body of a denture base having a predetermined form by polymerizing and hardening a polymethyl methacrylate resin;
(b) a step for coating and drying an adhesive agent on a body's inner surface to be in contact with a patient's alveolus ridge; said adhesive agent being prepared by dissolving a copolymer comprising an olefin and methyl methacrylate into a solvent; and
(c) a step for pressing and bonding a heated and softened lining layer on said surface coated by adhesive agent; said lining layer being made of an olefin thermoplastic elastomer or a mixture of said olefin thermoplastic elastomer and a thermoplastic elastomer comprising styrene-ethylene-butylene copolymer.

* * * * *